(12) United States Patent  
Silvis et al.

(10) Patent No.: US 7,559,262 B2
(45) Date of Patent: Jul. 14, 2009

(54) CVS SYSTEM SAMPLE WATER VAPOR MANAGEMENT

(75) Inventors: William Martin Silvis, Ann Arbor, MI (US); James Williamson, Whitmore Lake, MI (US)

(73) Assignee: AVL North America Inc., Plymouth, MI (US)

( * ) Notice: Subject to any disclaimer, the term of this patent is extended or adjusted under 35 U.S.C. 154(b) by 129 days.

(21) Appl. No.: 11/855,246

(22) Filed: Sep. 14, 2007

(65) Prior Publication Data

US 2008/0066565 A1 Mar. 20, 2008

Related U.S. Application Data

(60) Provisional application No. 60/845,271, filed on Sep. 15, 2006.

(51) Int. Cl.
*G01N 1/22* (2006.01)
(52) U.S. Cl. .................................. 73/863.01
(58) Field of Classification Search . 73/863.01–863.03, 73/863.51, 863.52, 863.71, 863.81, 863.84, 73/864, 864.02, 864.01, 864.21, 864.62
See application file for complete search history.

(56) References Cited

U.S. PATENT DOCUMENTS

| 5,821,435 | A | * | 10/1998 | Kojima | 73/863.01 |
| 6,405,577 | B2 | * | 6/2002 | Hanashiro et al. | 73/23.31 |
| 6,443,021 | B2 | * | 9/2002 | Hanashiro et al. | 73/863.11 |
| 6,490,937 | B2 | * | 12/2002 | Hanashiro et al. | 73/863.11 |

* cited by examiner

*Primary Examiner*—Hezron Williams
*Assistant Examiner*—Tamiko D Bellamy
(74) *Attorney, Agent, or Firm*—Carlson, Gaskey & Olds

(57) ABSTRACT

An exhaust sampling system is disclosed that includes a pre-fill gas source having a pre-fill gas. A sampling conduit is configured to collect exhaust gas and make-up gas. A sample bag is fluidly connected to the sampling conduit and the pre-fill gas source. A controller is programmed to run a test procedure in which a sample of exhaust gas and make-up gas is collected in the sample bag. The controller is configured to send a command that fills the sample bag with pre-fill gas prior to the test procedure. The pre-fill gas remains in the sample bag during the test procedure. The amount of pre-fill gas is selected to prevent the sample from condensing in the sample bag.

7 Claims, 2 Drawing Sheets

CVS SYSTEM SAMPLE WATER VAPOR MANAGEMENT

The present disclosure claims the benefits of U.S. Provisional Application No. 60/845,271, filed on Sep. 15, 2006, which is incorporated herein in its entirety by reference.

BACKGROUND

With traditional constant volume samplers (CVS), engine exhaust is diluted with ambient air and a small sample of the diluted exhaust is proportionally extracted and stored in one or more sample bags. Depending upon the engine size, drive cycle and ambient conditions, the CVS total flow rate, which includes both ambient air and engine exhaust, is selected to ensure the sample collected does not condense water when stored in the bags, or during subsequent analysis. This flow rate is determined by calculating the average dew point in the bag sample.

It is desirable to avoid water condensation within the sample bag for several reasons. First, condensation of water impacts the accuracy of the exhaust analysis. Some substances in the exhaust become soluble in water. These substances can be effectively "pulled out" of the exhaust so that they are not measured at the conclusion of the test. Also, the water vapor that becomes condensed is not measured and included in the test results. Second, the condensation can cause the collection of substances on the inside of the bag as the water subsequently evaporates thereby leaving an undesirable residue that will be present during future tests. Finally, new legislation requires no condensation in the sample bags.

There are several factors that make it difficult to avoid condensation of the sample within the bags. For example, use of alternative fuels, new test cycles and larger displacement engines all can lead to condensation within the sample bags. For example, if an aggressive test cycle is performed and the traditional optimal flow CVS flow rate is selected, then condensation will form. This is particularly true for test cycles where the maximum exhaust comes very early in the collection of the sample. The dew point of the sample may be higher than ambient conditions even though the average water concentration in the bag is less than ambient at the end of the cycle. CVS optimal flow rate is selected to ensure the average water concentration in the bags has a dew point less ambient temperature.

One potentially problematic test is the newly proposed US06 drive cycle. The cycle is 600 seconds long and the second sample bag used in the test will start filling 133 seconds into the drive cycle. The traditional desired flow rate is 1050 scfm when diluting a gas with a dew point of 18 deg C. For vehicles running on ethanol fuel, the ending dew point in the bag will be just above 23 deg C., with a peak dew point at the beginning of the second bag fill of 27 deg C. This is often higher than ambient conditions in a test cell. In this scenario, the CVS flow rate would typically be selected to dilute for the average bag dew point of 23 deg C., which would result in the sample condensing in the second sample bag due to the initial high peak.

In order to avoid condensation in the bag, the CVS flow rate would have to be raised to 2000 scfm to avoid the initial peak, which is undesirable. Increasing the CVS flow rate would reduce the already low concentration of exhaust within the sample making it more difficult to analyze. One approach that can be used to avoid condensation is to heat the bags, which would maintain the sample gas temperature above the maximum dew point and avoid the initial dew point peak. However, additional equipment must be employed for such an approach leading to a higher cost CVS.

What is needed is a CVS that avoids undesirably high peak dew points during test procedures without increasing the flow rate too high or adding significant cost to the system.

SUMMARY

An exhaust sampling system is disclosed that includes a pre-fill gas source having a pre-fill gas. A sampling conduit is configured to collect exhaust gas and make-up gas. A sample bag is fluidly connected to the sampling conduit and the pre-fill gas source. A controller is programmed to run a test procedure in which a sample of exhaust gas and make-up gas is collected in the sample bag. The controller is configured to send a command that fills the sample bag with pre-fill gas prior to the test procedure. The pre-fill gas remains in the sample bag during the test procedure. The amount of pre-fill gas is selected to prevent the sample from condensing in the sample bag.

These and other features of the disclosure can be best understood from the following specification and drawings, the following of which is a brief description.

DETAILED DESCRIPTION

Figure 1:
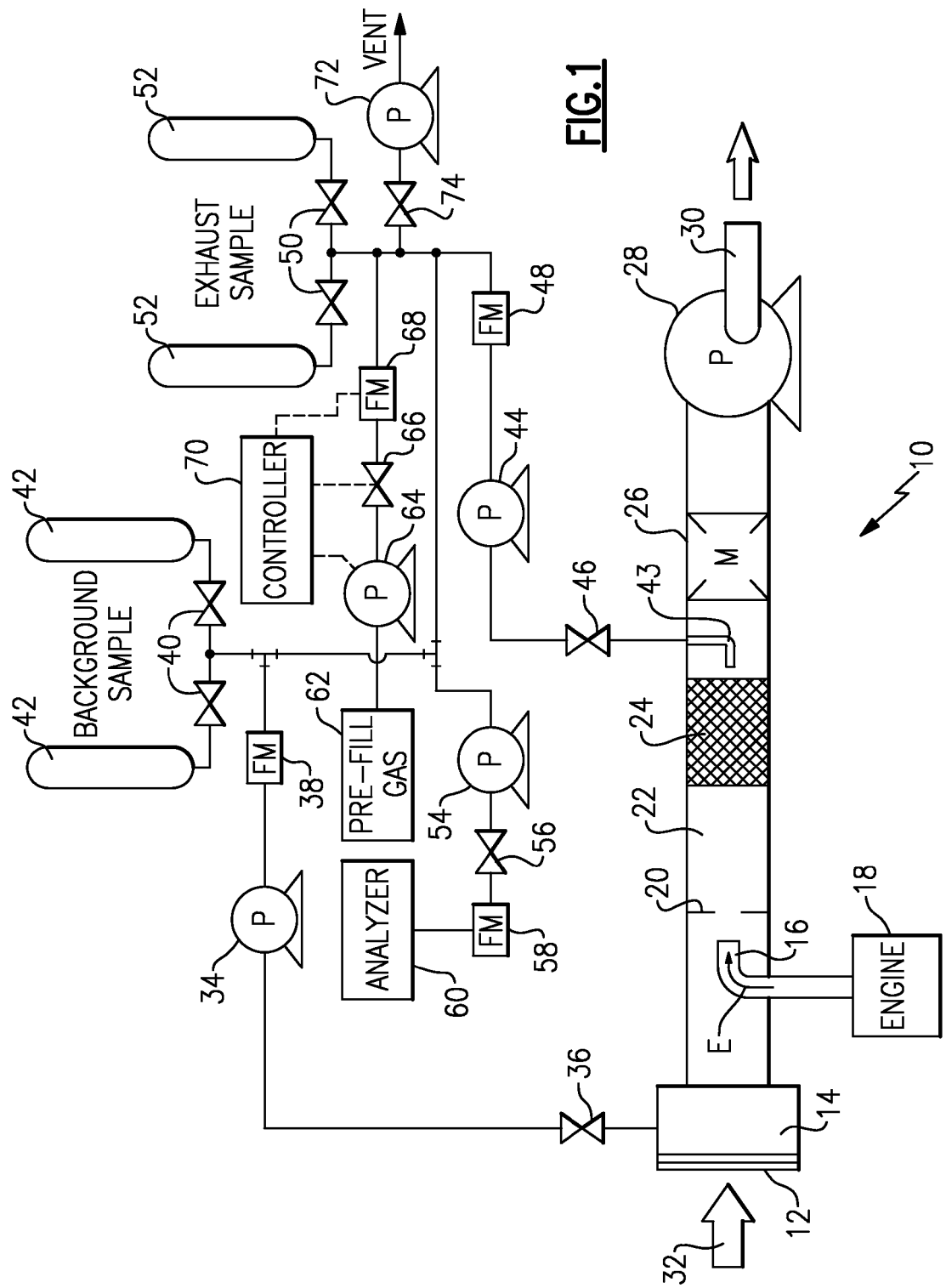
FIG. 1 is a highly schematic view of an example CVS including an example pre-fill gas system.

A highly schematic view of an exhaust sampling system 10 is shown in FIG. 1. The system 10 includes a make-up air inlet 12 that includes a filter 14. The inlet 12 provides make-up air 32 to a sampling conduit that also receives exhaust from a tailpipe 16 of an engine 18. The make-up air 32 and exhaust E pass through a mixing plate 20 to promote homogeneous mixing of the make-up air 32 and exhaust F as it flows through a tunnel 22 prior to sampling. A constant volume of the mixture is drawn through the sampling conduit by a pump 28. A heat exchanger 24 is used, in one example, to maintain the mixture at a desired temperature. The mixture is measured by a measuring device 26, prior to being expelled by the pump 28 through a discharge 30, to determine the quantity of mixture flowing through the sampling conduit. It should be understood that the system 10 is only exemplary and that many modifications can be made and still fall within the scope of the claims.

The engine 18 is run through a test procedure to determine the quantity of exhaust byproducts that the engine 18 produces. For the example system 10 shown, only a small portion of the exhaust E is sampled for subsequent analysis. As the amount of exhaust E produced by the engine 18 during the test procedure fluctuates, the make-up air 32 provides the remainder of the volume. The amount of byproducts in the sample is so small at times, that the components in the make-up air can impact the test results. To this end, a pump 34 draws an amount of make-up air into background bags 42 during the test procedure so that the effects of the make-up air can be taken into account. Valves 36, 40 regulate the flow of make-up air 32 into the background bags 42, and the flow meter 38 measures the amount of make-up air collected within the background bags 42.

A sampler 43 collects a small sample of the mixture for collecting into sample bags 52. One or more sample bags 52 may be used, and filling of the sample bags may be scheduled during various periods of the test procedure. A pump 44 draws the sample through a valve 46 and flow meter 48. Valves 50 regulate the filling of the sample bags 52. After the sample bags 52 have collected the samples, an analyzer 60 analyzes the contents of the sample bags 52 and 42 to determine the amount of various combustion byproducts. A pump 54 flows the sample through valve 56 and flow meter 58. It should be understood that more or fewer pumps, valves and flow meters than shown could be used.

A controller 70 communicates during the test procedure with the various pumps 28, 34, 54, 64, 72, valves 36, 40 46, 50, 56, 66, 74 and flow meters 38, 48, 58, 68 to obtain readings and direct their operation. All of the connections between the controller 70 and these components are not shown for clarity. In one example of this disclosure, one or more of the sample bags 52 is pre-filled with dry gas to prevent any peaks in dew point during the test procedure that would lead to undesired condensation. A source of pre-fill gas 62 is shown schematically in FIG. 1. An amount of pre-fill gas is pumped into one or more of the sample bags 52 prior to the collection of the exhaust sample. The controller 70 commands the pump 64 and valve 66 to fill a desired amount of pre-fill gas to a desired sample bag 52 to prevent condensation in the sample bag 52. The prefill may also incorporate other means to fill the bag such as a compressed air source. The flow meter 68 measures the amount of pre-fill gas.

Figure 2:
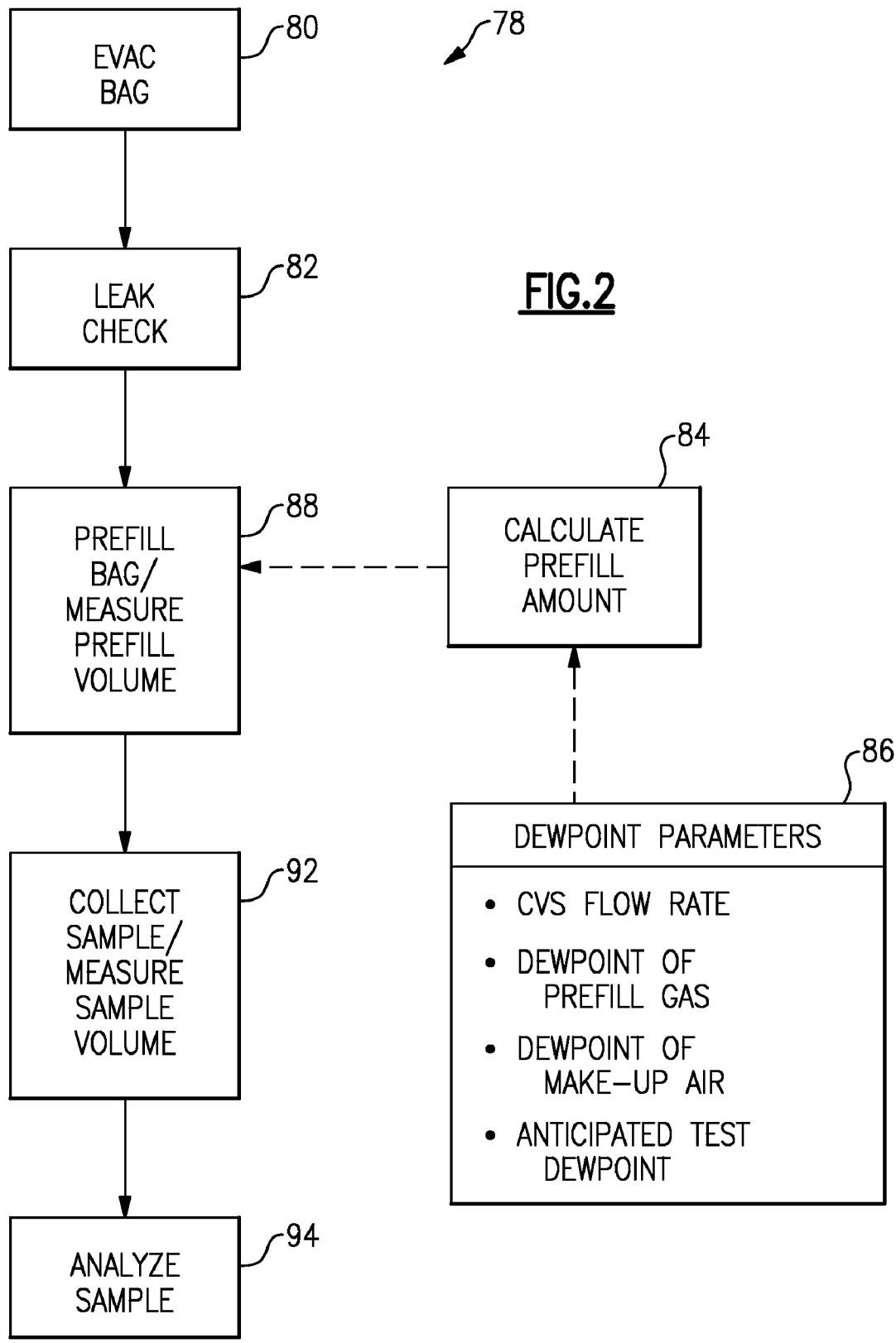
FIG. 2 is a flow chart depicting an example pre-fill procedure.

An example test procedure 78 according to the disclosure is shown in FIG. 2. The amount of pre-fill gas needed to prevent condensation is calculated at block 84 based upon one or more of the following (indicated at block 86): CVS test flow rate, dew point of the pre-fill gas, dew point of the make-up air, and anticipated test dew point within the sample bag 52. Calculations are performed based upon the various factors of each test to determine the minimum amount of pre-fill gas required to avoid condensation. This approach is desirable to minimize further dilution of the sample. The bags susceptible to condensation would be filled with dry clean air prior to the sampling (filling of the bag). According to this disclosure, the initial peak of wet gas is compensated for by the dry air, thus preventing condensation.

The sample bags 52 and ambient bags 42 are evacuated through vent 74 using pump 72 (FIG. 1), as indicated at block 80. The system 10 is leak checked (block 82), and the sample bag 52 is filled with a predetermined amount of pre-fill gas, as indicated at block 88. The amount of prefill gas is measured. The exhaust sample is collected and measured in the sample bag 52 during the test procedure with the pre-fill gas remaining in the sample bag 52, as indicated at block 92. As the sample bag 52 is filled during the test procedure, the dew point of the predetermined amount of pre-fill gas prevents the exhaust sample from condensing within the sample bag 52. The contents of the sample bag 52 and ambient bag 42 can then be analyzed to determine the amount of byproducts within the sample, as indicated at block 94.

In one example, the same "zero grade" or "instrument grade" air that is typically used to initially calibrate the system 10 can be used to pre-fill the sample bag 52. As a result, the pre-fill feature can be incorporated into a traditional CVS with very little modification and expense. Alternatively, ambient air can be used to pre-fill the sample bag 52. Using ambient air may be desirable since it makes accounting for the pre-fill air's affects at the analysis stage of the test sampler. The analytical equations set forth in the Code of Federal Regulations for test procedures are such that accounting for pre-fill ambient air is more straightforward. Using zero grade air instead of ambient air requires modifications to those equations, which may be undesired by some customers. It should be understood, however, that any number of suitable substances may be used to pre-fill the sample bags 52.

Although an example embodiment has been disclosed, a worker of ordinary skill in this art would recognize that certain modifications would come within the scope of the claims. For that reason, the following claims should be studied to determine their true scope and content.

What is claimed is:

1. An exhaust sampling system comprising:
   a pre-fill gas source having a pre-fill gas;
   a sampling conduit configured to collect exhaust gas and make-up gas;
   a sample bag fluidly connected to the sampling conduit and the pre-fill gas source; and
   a controller programmed to run a test procedure in which a sample of the exhaust gas and make-up gas is collected in the sample bag, the controller configured to send a command that fills the sample bag with a desired amount of pre-fill gas prior to the test procedure, with the pre-fill gas remaining in the sample bag during the test procedure.

2. The exhaust sampling system according to claim 1, comprising a pump, the controller programmed to direct the pump to evacuate the sample bag prior to sending the command.

3. The exhaust sampling system according to claim 1, comprising a pump, the controller sending the command to the pump to pre-fill the sample bag.

4. The exhaust sampling system according to claim 1, comprising a pump, the controller programmed to direct the pump to fill the sample bag with the sample during the tests procedure.

5. The exhaust sampling system according to claim 1, comprising a filter and tailpipe fluidly connected to the sampling conduit, the filter and tailpipe configured to respectively provide the make-up gas and exhaust gas.

6. The exhaust sampling system according to claim 1, wherein the desired amount of pre-fill gas corresponds to volume of pre-fill gas maintaining a dew point within the sample bag during the test procedure below an undesired dew point.

7. The exhaust sampling system according to claim 6, wherein the desired amount of pre-fill gas is calculated based upon at least one of a CVS test flow rate, a dew point of the pre-fill gas, a dew point of the make-up gas, and an anticipated test dew point.

* * * * *